United States Patent
Sato

(10) Patent No.: US 11,484,237 B2
(45) Date of Patent: Nov. 1, 2022

(54) PHYSIOLOGICAL INFORMATION MEASUREMENT APPARATUS AND PROGRAM

(71) Applicant: NIHON KOHDEN CORPORATION, Tokyo (JP)

(72) Inventor: Makoto Sato, Tokorozawa (JP)

(73) Assignee: NIHON KOHDEN CORPORATION, Tokyo (JP)

( * ) Notice: Subject to any disclaimer, the term of this patent is extended or adjusted under 35 U.S.C. 154(b) by 288 days.

(21) Appl. No.: 16/159,810

(22) Filed: Oct. 15, 2018

(65) Prior Publication Data

US 2019/0117098 A1 Apr. 25, 2019

(30) Foreign Application Priority Data

Oct. 24, 2017 (JP) .............................. JP2017-205251

(51) Int. Cl.
| | |
|---|---|
| *A61B 5/00* | (2006.01) |
| *A61B 5/377* | (2021.01) |
| *A61B 5/24* | (2021.01) |
| *A61N 1/04* | (2006.01) |
| *A61N 1/36* | (2006.01) |

(Continued)

(52) U.S. Cl.
CPC .............. *A61B 5/24* (2021.01); *A61N 1/0404* (2013.01); *A61N 1/36* (2013.01); *A61B 5/125* (2013.01); *A61B 5/38* (2021.01); *A61B 5/4836* (2013.01); *A61B 5/7221* (2013.01); *A61B 5/7235* (2013.01)

(58) Field of Classification Search
CPC ....... A61B 5/04; A61B 5/04018; A61B 5/125; A61B 5/04004; A61B 5/7221; A61B 5/044; A61B 5/12; A61N 1/36
See application file for complete search history.

(56) References Cited

U.S. PATENT DOCUMENTS 5,609,158 A * 3/1997 Chan ..................... A61B 5/0464
600/518
6,331,162 B1 * 12/2001 Mitchell ............... A61B 5/0285
600/485

(Continued)

FOREIGN PATENT DOCUMENTS

| | | |
|---|---|---|
| JP | H11-123181 A | 5/1999 |
| JP | 2005-237867 A | 9/2005 |

(Continued)

OTHER PUBLICATIONS

Machine translation of Patent No. WO-2013001836-A1, retrieved from patentscope.wipo.int, on Oct. 22, 2020 (Year: 2013).*

(Continued)

*Primary Examiner* — Etsub D Berhanu
(74) *Attorney, Agent, or Firm* — Pearne & Gordon LLP

(57) ABSTRACT

A physiological information measurement apparatus includes a measuring section that acquires a physiological signal from a living body of a subject, a signal processor that produces a plurality of physiological signal waveforms based on the physiological signal acquired from the measuring section, and that identifies an arithmetic average waveform that is obtained by arithmetic averaging of the plurality of physiological signal waveforms, and information relating to arithmetic average dispersion, and a display that displays at least the information relating to the arithmetic average dispersion.

9 Claims, 7 Drawing Sheets

(51) Int. Cl.
   *A61B 5/12*   (2006.01)
   *A61B 5/38*   (2021.01)

(56) References Cited

U.S. PATENT DOCUMENTS

| | | |
|---|---|---|
| 2005/0192492 A1 | 9/2005 | Cho et al. |
| 2006/0276719 A1* | 12/2006 | Litvak ................... A61B 5/24 600/544 |
| 2009/0192745 A1* | 7/2009 | Kamath ............... A61B 5/7475 702/85 |
| 2014/0254903 A1 | 9/2014 | Poole et al. |
| 2017/0245775 A1* | 8/2017 | Hyodo ................. A61B 5/316 |

FOREIGN PATENT DOCUMENTS

| | | | | |
|---|---|---|---|---|
| JP | WO-2013001836 A1 * | 1/2013 | ............. | A61B 5/125 |
| JP | 2014-171883 A | 9/2014 | | |
| JP | 2017-148404 A | 8/2017 | | |
| WO | WO-03000128 A2 * | 1/2003 | ............. | A61B 5/369 |

OTHER PUBLICATIONS

Board of ME Technical Education in Japanese Society for Medial and Biological Engineering, Fundamental knowledge and safety control of ME, 5th edition, Kabushiki Kaisha Nankodo, Dec. 10, 2008, p. 150 to 153.
Japanese Office Action dated Jun. 15, 2021 issued in Japan Patent Application No. 2017-205251.

\* cited by examiner

PHYSIOLOGICAL INFORMATION MEASUREMENT APPARATUS AND PROGRAM

CROSS REFERENCE TO RELATED APPLICATION

This application is based on Japanese Patent Applications No. 2017-205251 filed on Oct. 24, 2017, the contents of which are incorporated herein by reference.

BACKGROUND

The disclosure relates to a physiological information measurement apparatus and a program for arithmetically averaging physiological signal waveforms produced from a physiological signal.

In a physiological information measurement apparatus for measuring a somatosensory evoked potential (SEP), a brainstem auditory evoked potential (BAEP), a visual evoked potential (VEP), an auditory brainstem response (ABR), or the like, a physiological signal such as an electroencephalogram is measured.

Non-patent Literature, Board of ME Technical Education in Japanese Society for Medial and Biological Engineering, Fundamental knowledge and safety control of ME, 5$^{th}$ edition, Kabushiki Kaisha Nankodo, Dec. 10, 2008, p. 150 to 153 discloses a cerebral evoked potentiometer which, mainly from the scalp, detects minute potential changes that are evoked in respective sensory areas of the cerebrum in response to stimulation to the visual sense and the like. The evoked minute potentials contain a visual evoked potential (VEP) evoked by stimulation of flash light or pattern light, a somatosensory evoked potential (SEP) obtained by electrically stimulating a peripheral sensory nerve, a long-latency auditory evoked potential (AEP) evoked by stimulation of tone burst or clicking sound, an auditory brainstem response (ABR), and the like. These potentials are minute potentials which vary in a range from about 0.1 to 10 µV, and which are buried within an electroencephalogram signal.

An electroencephalogram signal containing evoked potentials is subjected to an A/D conversion, and then to arithmetic averaging in synchronization with stimulation. The arithmetic averaging is performed in order to eliminate influences of noises to correctly detect a minute physiological signal.

In arithmetic averaging of usual physiological signals such as a somatosensory evoked potential (SEP), a brainstem auditory evoked potential (BAEP), a visual evoked potential (VEP), or an auditory brainstem response (ABR), arithmetic averaging is performed a predetermined number of times.

However, the kinds of noises that are superimposed on the signal during measurement, and the manner in which the noises are superimposed are varied depending on the measurement environment. Even when arithmetic averaging is performed a predetermined number of times, therefore, there is a case where the number of times at which arithmetic averaging is performed (hereinafter, the number is referred to as the arithmetic averaging number) is not sufficiently large, or the arithmetic averaging number is larger than necessary.

This matter is not limited to inspections of the above-described evoked potentials such as an SEP, and may occur also in an electrocardiogram inspection using a late ventricular potential. Namely, this is common to physiological information measurement apparatuses in which arithmetic averaging is performed.

In a conventional apparatus in which arithmetic averaging is performed in the above-described manner, a situation where the arithmetic averaging number is excessive or deficient may easily occurs. Conventionally, however, no configuration for providing an index indicating an excessive or deficient arithmetic averaging number exists.

The present disclosure presents an index for performing an arithmetic averaging with an adequate number of times.

SUMMARY OF THE INVENTION

According to an aspect of the invention, a physiological information measurement apparatus includes a measuring section that acquires a physiological signal from a living body of a subject, a signal processor that produces a plurality of physiological signal waveforms based on the physiological signal acquired from the measuring section, and that identifies an arithmetic average waveform that is obtained by arithmetic averaging of the plurality of physiological signal waveforms, and information relating to arithmetic average dispersion, and a display that displays at least the information relating to the arithmetic average dispersion.

According to the configuration, information relating to arithmetic average dispersion is displayed, and therefore an index for setting the arithmetic averaging number to an adequate number can be visualized.

According to another aspect of the invention, a physiological information measurement apparatus includes a measuring section that acquires a physiological signal from a living body of a subject, a signal processor that produces a plurality of physiological signal waveforms based on the physiological signal acquired from the measuring section, and that identifies an arithmetic average waveform that is obtained by arithmetic averaging of the plurality of physiological signal waveforms, and information relating to arithmetic average dispersion, and a determination section that determines whether the number of times of the arithmetic averaging is sufficient or not, based on the information relating to the arithmetic average dispersion.

According to the configuration, it is determined whether the arithmetic averaging number is sufficient or not, based on the information relating to arithmetic average dispersion, and therefore it is possible to know whether the arithmetic averaging number is sufficient or not.

According to another aspect of the invention, a computer readable medium stores a physiological information measurement program causing a computer to execute a process. The process includes producing a plurality of physiological signal waveforms based on a physiological signal acquired from a living body of a subject, identifying an arithmetic average waveform that is obtained by arithmetic averaging of the plurality of physiological signal waveforms, and information relating to arithmetic average dispersion, and displaying the information relating to the arithmetic average dispersion.

According to the program, the function of displaying the information relating to arithmetic average dispersion is realized, and therefore an index for setting the arithmetic averaging number to an adequate number can be visualized.

According to the disclosure, it is possible to present an index for setting an arithmetic averaging number to an adequate number.

DETAILED DESCRIPTION OF EMBODIMENTS

Hereinafter, embodiments of the physiological information measurement apparatus of the disclosure will be described with reference to the drawings.

First Embodiment, Display Device

The physiological information measurement apparatus of the disclosure may be configured in any manner as far as it is an apparatus for arithmetically averaging electric (potential) signals obtained from a living body. Hereinafter, an evoked potential measurement apparatus 1 which is used in measurement of an auditory brainstem response (hereinafter, abbreviated as "ABR") will be described as an example of the physiological information measurement apparatus.

Figure 1:
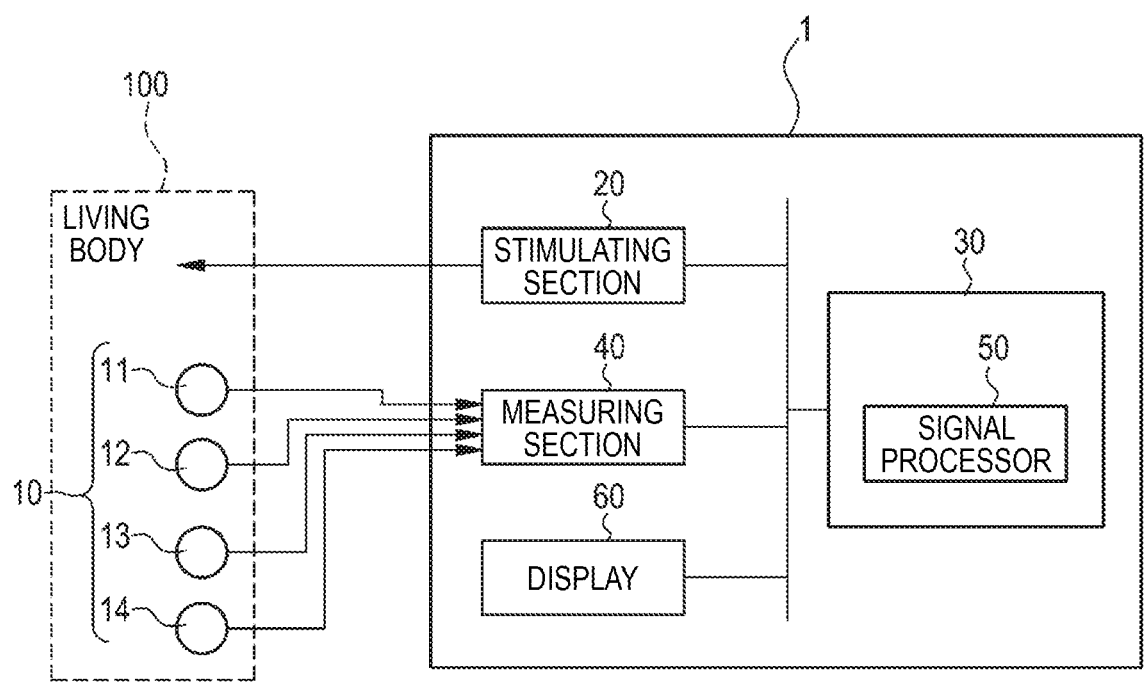
FIG. 1 is a functional block diagram of an evoked potential measurement apparatus which is an embodiment of the disclosure.

The evoked potential measurement apparatus 1 is configured so as to acquire physiological signals (electric signals) from a living body 100 of a subject. The physiological signals are acquired through various devices suitable for measurement, such as electrodes, probes, and cuffs which are attached to the living body 100. As shown in FIG. 1, the evoked potential measurement apparatus 1 of the embodiment uses a lead electrode section 10. The lead electrode section 10 is configured by a plurality of electrodes 11 to 14 which are to be attached to the living body 100 of the subject. The lead electrode section 10 is configured so as to acquire exogenous evoked potentials in response to stimulation which is applied by a stimulating section 20, from the living body 100. The number of the electrodes constituting the lead electrode section 10 can be adequately determined in accordance with the measurement object and the measurement portion. As shown in FIG. 1, the lead electrode section 10 in the embodiment is configured by the four electrodes 11 to 14.

The evoked potential measurement apparatus 1 has the stimulating section 20, a controller 30, a measuring section 40, and a display 60.

The stimulating section 20 is configured so as to apply stimulation such as visual, auditory, or somatosensory stimulation to the living body 100. In the embodiment, the stimulating section 20 is configured so as to apply clicking sound (sound stimulation) to the living body 100.

The measuring section 40 is configured so as to acquire evoked potentials (analog physiological signals) produced in the living body 100. In the embodiment, the measuring section 40 acquires evoked potentials which are produced in the living body 100 in response to stimulation applied by the stimulating section 20, through the electrodes 11 to 14. The physiological signals acquired by the measuring section 40 are converted to digital data by an A/D converter or the like which is not illustrated. The physiological signals which have been converted to digital data are supplied to the controller 30.

The controller 30 includes a signal processor 50. The controller 30 is configured so as to produce a control signal relating to the stimulation application, in accordance with the application timing and intensity of the stimulation which is supplied from an operation content supplying section that is not shown. The control signal is output from the controller 30 to the stimulating section 20.

The controller 30 includes a memory and a processor.

The memory is configured so as to store computer readable instructions (programs). The memory is configured, for example, by a ROM (Read Only Memory) which stores various programs (programs relating to measurement, those relating to signal processing, and those relating to determination) and the like, a RAM (Random Access Memory) having work areas in which various programs to be executed by the processor, and the like are stored, etc.

The processor is, for example, a CPU (Central Processing Unit), an MPU (Micro Processing Unit), and or a GPU (Graphics Processing Unit), and is configured so as to develop a designated one of the various programs installed in the ROM, in the RAM, and execute various processes in cooperation with the RAM.

The signal processor 50 is configured so as to perform signal processing of the physiological signals (digital data) acquired from the measuring section 40.

The signal processor 50 produces a plurality of physiological signal waveforms based on the acquired physiological signals. The signal processor 50 adds up the plurality of physiological signal waveforms, and averages the whole added physiological signal waveforms to produce an arithmetic average waveform. The signal processor 50 is further configured so as to perform a process of identifying information relating to arithmetic average dispersion. In the embodiment, the signal processor 50 produces a plurality of ABR waveforms based on the physiological signals supplied from the measuring section 40. The signal processor 50 arithmetically averages the plurality of ABR waveforms to produce an arithmetic average waveform. The signal processor 50 identifies information relating to arithmetic average dispersion.

The signal processor 50 is configured so as to output the arithmetic average waveform and the information relating to arithmetic average dispersion to the display 60.

The display 60 is electrically connected to the signal processor 50. The display 60 is configured so as to display the arithmetic average waveform and information relating to arithmetic average dispersion which are output from the signal processor 50, in a manner in which the user can view the waveform and the information. For example, the display 60 may be a liquid crystal display device having a screen on which the graphs of FIGS. 2 to 4 can be displayed. The display may be performed not only in the form of waveforms, but also in various other forms in which the user can view the display, such as numerals, characters, or symbols.

Figure 2:
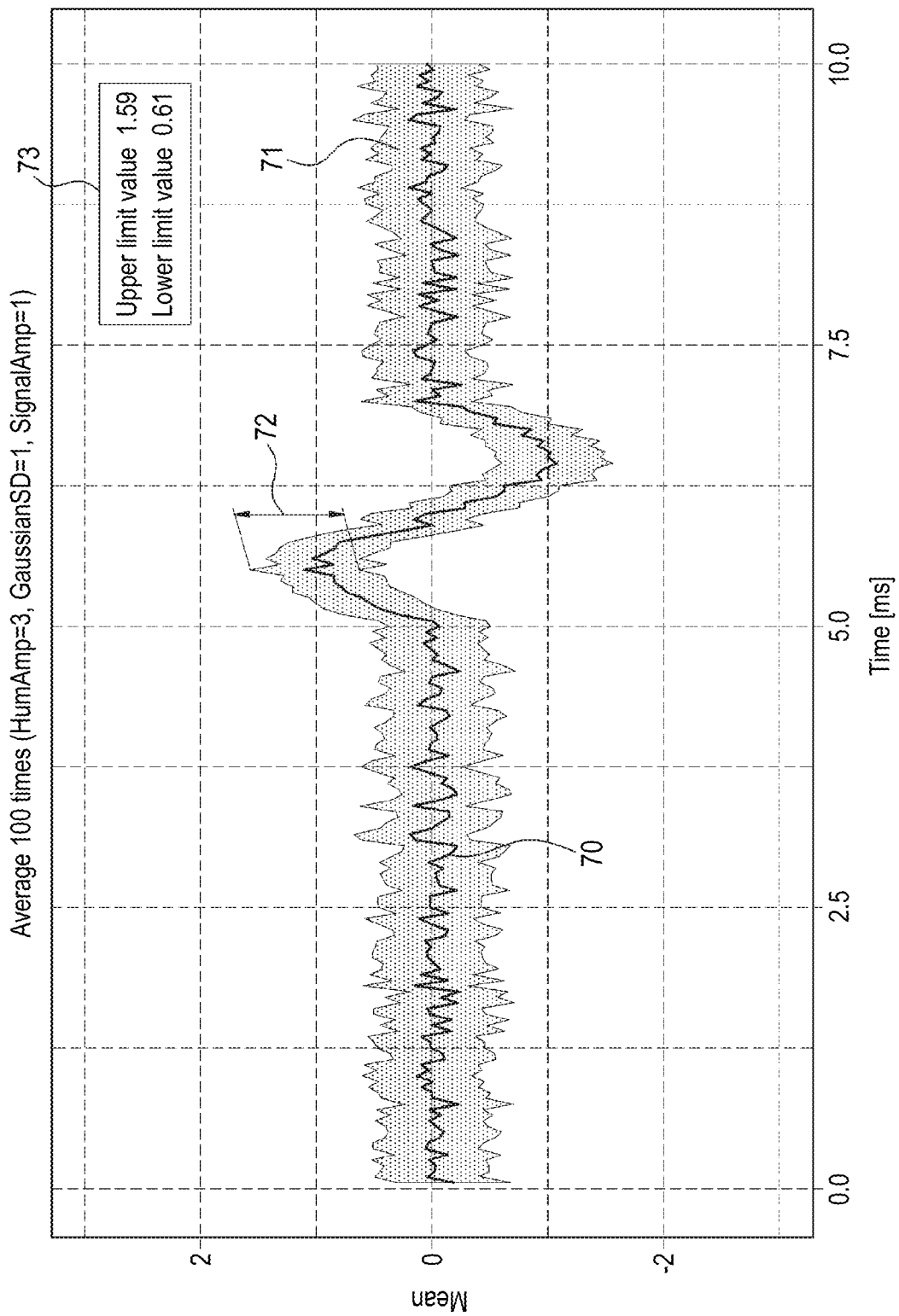
FIG. 2 is a view illustrating an arithmetic average waveform and arithmetic average dispersion relating to a simulated measurement of an auditory brainstem response (ABR).

Referring to FIG. 2, an arithmetic average waveform and information relating to arithmetic average dispersion will be described in detail. FIG. 2 illustrates an example of a display of an arithmetic average waveform and arithmetic average dispersion relating to a simulated measurement of an ABR measurement. FIG. 2 is a view of an ABR simulated measurement where waveforms in which, at 5 ms, a sinusoidal waveform having an amplitude of 1 appears in one cycle are arithmetically averaged 100 times. The conditions of the simulated measurement of FIG. 2 are as follows. Stimulation is performed at 13 Hz, it is assumed that hum noise at 50 Hz (amplitude=3) is superimposed, and Gaussian noise is added with a standard deviation of 1 while simulating noise of an amplifier.

Here, an arithmetic average waveform means a waveform which is obtained as a result of arithmetic averaging of physiological signal waveforms. In other words, an arithmetic average waveform is a waveform which is obtained as a result of plotting mean values of a plurality of physiological signal waveforms. In FIG. 1, an arithmetic average waveform 70 is illustrated.

Arithmetic average dispersion is an index which is determined for each time period when sampling is performed, and means a range where a plurality of waveforms which are measured for the purpose of addition are possible. Arithmetic average dispersion is an index indicating whether a statistically significant result is obtained or not in executed arithmetic averaging. Arithmetic average dispersion can be expressed, for example, by using a confidence interval, a standard deviation (SD), dispersion, or the like. As an example of arithmetic average dispersion, a confidence interval 71 of a confidence coefficient of 95% is illustrated in FIG. 2. Hereinafter, "confidence interval of a confidence coefficient of 95%" is referred to merely as "95% confidence interval" or "95% CI."

Arithmetic average dispersion will be described in more detail with reference to FIGS. 2 to 4.

Figure 3:
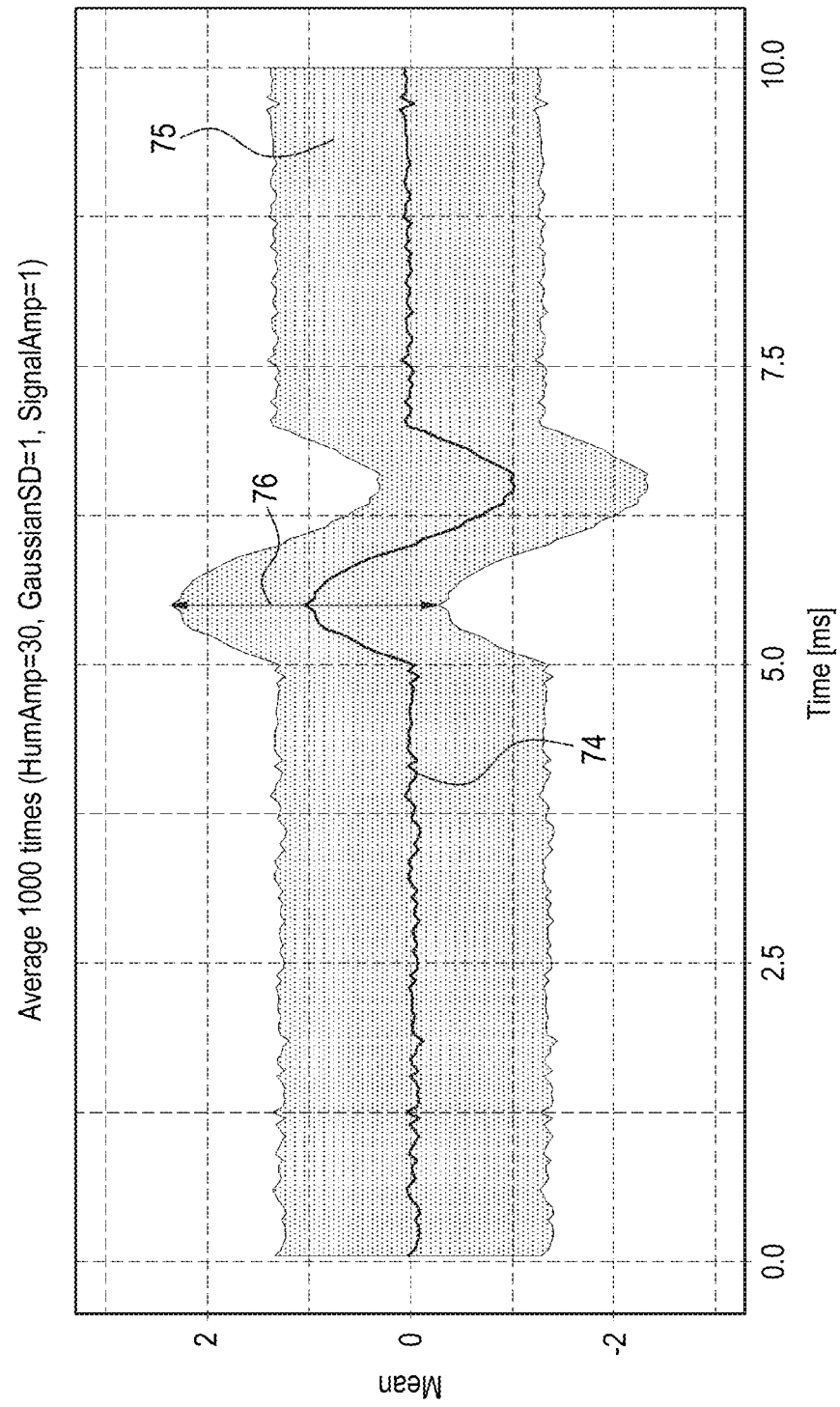
FIG. 3 is a view illustrating an arithmetic average waveform and arithmetic average dispersion relating to a simulated measurement of an auditory brainstem response (ABR).

FIG. 3 illustrates an example of a display of an arithmetic average waveform and arithmetic average dispersion relating to a simulated measurement of an ABR measurement in which arithmetic averaging is performed 100 times while the amplitude of hum noise is set to 30, and the other conditions are identical with those of the case of FIG. 2. FIG. 3 is a view of a simulated measurement where the arithmetic averaging number (the number of times at which arithmetic averaging is performed) is larger than that in the simulated measurement of FIG. 2, but more noise is contained as compared with the simulated measurement of FIG. 2.

In FIG. 3, an arithmetic average waveform 74 is illustrated. Moreover, a 95% CI 75 is illustrated as information relating to arithmetic average dispersion.

The 95% CI 71 of FIG. 2, and the 95% CI 75 of FIG. 3 are compared with each other. At the places where the arithmetic average waveform 70 of FIG. 2, and the arithmetic average waveform 74 of FIG. 3 have the respective maximum values on the time axis, when the width (the difference between the upper limit value and the lower limit value) 72 of the 95% CI 71, and the width 76 of the 95% CI 75 are compared with each other, the width 76 of the 95% CI 75 is larger than the width 72 of the 95% CI 71. Also in the whole range of the time axis, similarly, the width of the 95% CI 75 is larger than that of the 95% CI 71. A large width of a confidence interval means that, even when arithmetic averaging is performed, there is a possibility that noise components (noise) cannot be sufficiently eliminated, and the waveform of the original signal component is not obtained. When attention is given only to the arithmetic average waveform 74 of FIG. 3, namely, it seems that the waveform indicating the original signal component (the waveform which is set in the simulated measurement, and in which, at 5 ms, a sinusoidal waveform having an amplitude of 1 appears in one cycle) is obtained. However, the width of the 95% CI 75 of FIG. 3 is wider than that of the 95% CI 71 of FIG. 2. The arithmetic average waveform 74 is obtained by adding up waveforms of the simulated measurement, and then plotting mean values. Therefore, FIG. 3 is a view in which the waveform (a sinusoidal waveform having an amplitude of 1) indicating the original signal component is not obtained, and it cannot be statistically denied that a false positive in which a zero (flat) waveform appears is produced.

By contrast, it seems that the arithmetic average waveform 70 of FIG. 2 is a waveform in which fine disturbances exist in the amplitude as compared with the arithmetic average waveform 74 of FIG. 3, and which is dirty.

However, the width of the 95% CI 71 illustrated in FIG. 2 is narrower than that of the 95% CI 75 illustrated in FIG. 3 in the whole range of the time axis.

From the narrowness of the width of the 95% CI 71 of FIG. 2, it is known that a statistically significant waveform can be confirmed in FIG. 2, and it is seen that further arithmetic averaging is unnecessary. Namely, it is known that the arithmetic average waveform 70 is obtained by performing arithmetic averaging an adequate number of times, and it is seen that further addition is unnecessary.

Figure 4:
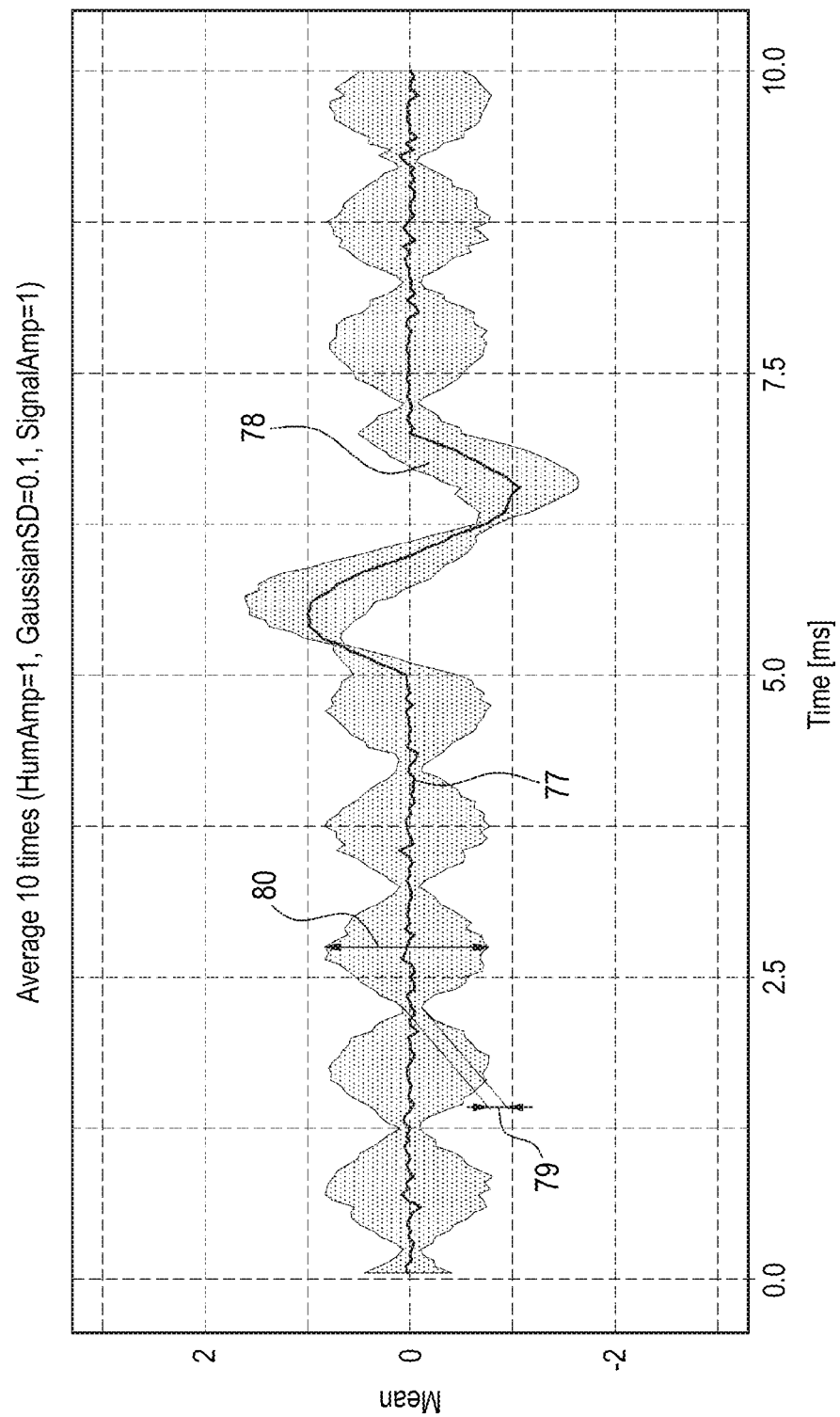
FIG. 4 is a view illustrating an arithmetic average waveform and arithmetic average dispersion relating to a simulated measurement of an auditory brainstem response (ABR).

FIG. 4 illustrates an example of a display of an arithmetic average waveform and arithmetic average dispersion relating to an ABR simulated measurement in which the amplitude of hum noise is set to 1, Gaussian noise is added with a standard deviation of 0.1 while simulating noise of an amplifier, and arithmetic averaging is performed ten times. FIG. 4 is a view of the simulated measurement in which hum noise and noise of the amplifier are reduced as compared with the simulated measurement of FIG. 2, and the arithmetic averaging number is made smaller than 100 times of FIG. 2.

In FIG. 4, an arithmetic average waveform 77 is illustrated. Moreover, a 95% CI 78 is illustrated as information relating to arithmetic average dispersion.

In the 95% CI 78 of FIG. 4, the width of the 95% CI 78 at a place indicated by the reference numeral 79 is narrower than that of the 95% CI 78 at a place indicated by the reference numeral 80. The width of the 95% CI 78 of FIG. 4 is largely varied in the whole range of the time axis. In the 95% CI 78, it is seen that, at places where the width is large, such as the place indicated by the reference numeral 80, noise is contained more largely than that at places where the width is small such as the place indicated by the reference numeral 79.

When, as illustrated in FIGS. 2 to 4, the 95% CI 71, 75, or 78 and the arithmetic average waveform 70, 74, or 77 are displayed in a common area, arithmetic average dispersion can be more clearly known. Namely, the arithmetic average waveform 70, 74, or 77 and the 95% CI 71, 75, or 78 which is arithmetic average dispersion are superimposedly displayed in one graph, whereby the wideness or narrowness of the width of the 95% CI 71, 75, or 78 (for example, the width 72 of the 95% CI 71, the width 76 of the 95% CI 75, and the widths of the 95% CI 78 at the places indicated by the reference numerals 79 and 80) which is arithmetic average dispersion can be more clearly known with reference to the arithmetic average waveform 70, 74, or 77. When the wideness/narrowness of the width of the 95% CI 71, 75, or 78 is subjected to comparison in the whole range of the time axis of the graph, it is possible to visualize the pattern of the super imposition of noise in the whole range of the time axis.

The information relating to arithmetic average dispersion has various modes. For example, the information relating to arithmetic average dispersion includes numerical data of the width of a 95% CI, numerical information of the standard deviation, and the like. The numerical data of the width of a 95% CI include the upper and lower limit values in a confidence interval, and the like. Numerical information 73 illustrated in FIG. 2 indicates the upper limit value of 1.59 and lower limit value of 0.61 at the place indicated by the width 72 of the 95% CI 71 illustrated in FIG. 2.

Next, the measurement by the evoked potential measurement apparatus 1, and the display of arithmetic average dispersion will be described.

The inspector attaches the electrodes 11 to 14 of the lead electrode section 10 to the living body 100. A headphone which provides clicking sound (sound stimulation) is attached to the living body 100. The inspector operates an operating section which is not illustrated, to input various set values such as the stimulation intensity (sound pressure level) of clicking sound which is to be applied to the living body 100, and the application timing of the clicking sound, to the controller 30. In accordance with the various input set values, the controller 30 produces a control signal regarding to stimulation application. The controller 30 outputs the produced control signal to the stimulating section 20. The stimulating section 20 applies clicking sound corresponding to the control signal, to the living body 100 through the headphone.

Potential differences which are produced in the electrodes 11 to 14 of the lead electrode section 10 in accordance with the application of the clicking sound are supplied from the electrodes 11 to 14 to the measuring section 40. The measuring section 40 acquires the potential differences (analog physiological signals), converts the acquired physiological signals to digital data, and outputs the convened physiological signal (digital data) to the signal processor 50. The signal processor 50 produces physiological signal waveforms based on the physiological signals. The signal processor 50 performs arithmetic averaging of the physiological signal waveforms, and produces an arithmetic average waveform. Moreover, the signal processor 50 identifies information relating to arithmetic average dispersion. The signal processor 50 outputs the arithmetic average waveform and the information relating to arithmetic average dispersion, to the display 60. The display 60 displays the arithmetic average waveform and information relating to arithmetic average dispersion which are supplied from the signal processor 50.

Figure 5:
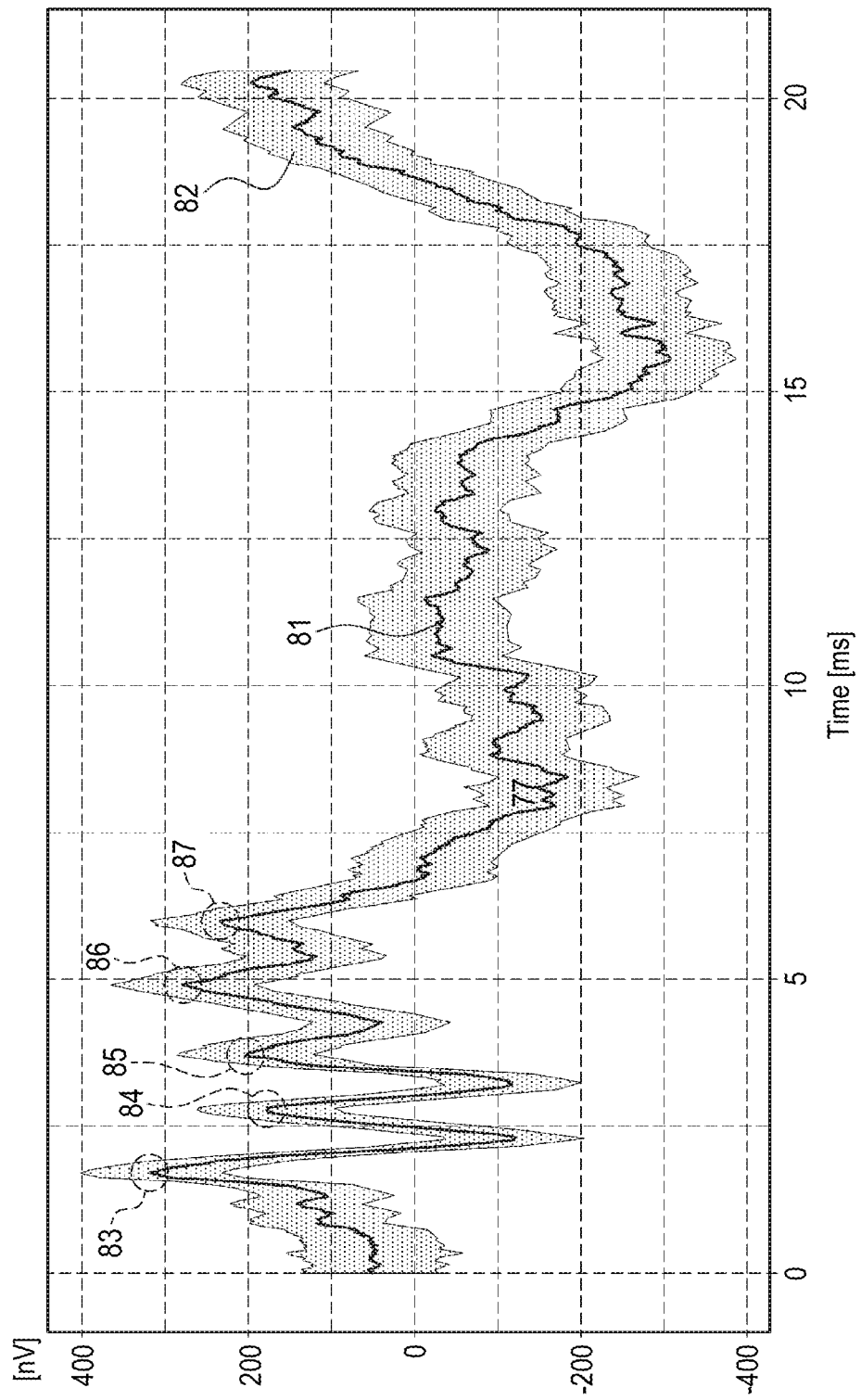
FIG. 5 is a view illustrating an arithmetic average waveform and arithmetic average dispersion relating to a simulated measurement of an auditory brainstem response (ABR).
Figure 6:
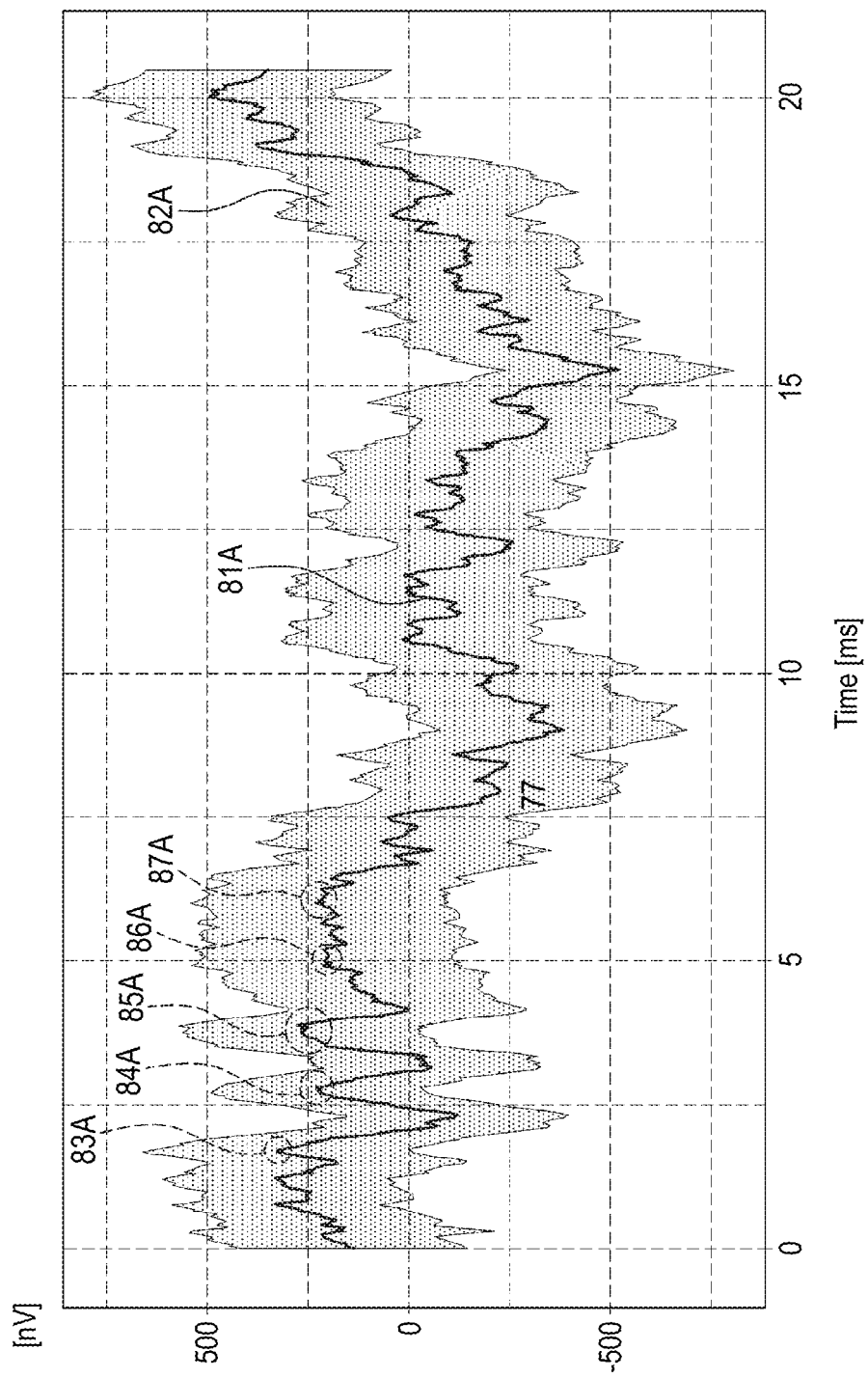
FIG. 6 is a view illustrating an arithmetic average waveform and arithmetic average dispersion relating to a simulated measurement of an auditory brainstem response (ABR).

Examples in which the arithmetic average waveform and information relating to arithmetic average dispersion in an actual measurement are displayed on the display 60 are illustrated in FIGS. 5 and 6, respectively. FIG. 5 is a view illustrating an arithmetic average waveform and information relating to arithmetic average dispersion that are pertinent to an ABR measurement in which arithmetic averaging is performed 1,000 times. FIG. 6 is a view illustrating an arithmetic average waveform and information relating to arithmetic average dispersion that are pertinent to an ABR measurement in which arithmetic averaging is performed 100 times. The method of the ABR measurements of FIGS. 5 and 6 is similar to that performed in a usual ABR measurement, and therefore its description is omitted.

FIG. 5 illustrates an arithmetic average waveform 81 and 95% CI 82 in an ABR. In the arithmetic average waveform 81, the reference numeral 83 indicates a first wave, and the width of the 95% CI 82 of the first wave is 171. In the arithmetic average waveform 81, the reference numeral 84 indicates a second wave, and the width of the 95% CI 82 of the second wave is 165. In the arithmetic average waveform 81, the reference numeral 85 indicates a third wave, and the width of the 95% CI 82 of the third wave is 165. In the arithmetic average waveform 81, the reference numeral 86 indicates a fourth wave, and the width of the 95% CI 82 of the fourth wave is 171. In the arithmetic average waveform 81, the reference numeral 87 indicates a fifth wave, and the width of the 95% CI 82 of the fifth wave is 165. Since the widths of the 95% CI 82 relating to the arithmetic average waveform 81 of the first to fifth waves are narrow, it can be known that the arithmetic averaging number is sufficient.

FIG. 6 illustrates an arithmetic average waveform 81A and 95% CI 82A in an ABR. In the arithmetic average waveform 81A, the reference numeral 83A indicates a first wave, and the width of the 95% CI 82A of the first wave is 655. In the arithmetic average waveform 81A, the reference numeral 84A indicates a second wave, and the width of the 95% CI 82A of the second wave is 524. In the arithmetic average waveform 81A, the reference numeral 85A indicates a third wave, and the width of the 95% CI 82A of the third wave is 595. In the arithmetic average waveform 81A, the reference numeral 86A indicates a fourth wave, and the width of the 95% CI 82A of the fourth wave is 643. In the arithmetic average waveform 81A, the reference numeral 87A indicates a fifth wave, and the width of the 95% CI 82A of the fifth wave is 631. Since the widths of the 95% CI 82A relating to the arithmetic average waveform 81 of the first to fifth waves are wide, it can be known that the arithmetic averaging number of the arithmetic average waveform 81A illustrated in FIG. 6 is insufficient.

Moreover, the 95% CI illustrated in FIG. 5, and the 95% CI illustrated in FIG. 6 are compared with each other in the whole range of the time axis.

The 95% CI 82 illustrated in FIG. 5 is within a width of about 200 nV in the whole range of the time axis. For example, the widths of the 95% CI 82 of the first to fifth waves illustrated in FIG. 5 are from 165 to 171.

By contrast, the 95% CI 82A illustrated in FIG. 6 exhibits a width which exceeds 500 nV, in the whole range of the time axis. For example, the widths of the 95% CI 82A of the first to fifth waves illustrated in FIG. 6 are from 524 to 655.

Since the width of the 95% CI 82 in the whole range of the time axis is narrow, it can be known that the arithmetic averaging number of the arithmetic average waveform 81 illustrated in FIG. 5 is sufficient.

By contrast, since the width of the 95% CI 82A in the whole range of the time axis is wide, it can be known that the arithmetic averaging number of the arithmetic average waveform 81A illustrated in FIG. 6 is insufficient.

In the arithmetic average waveform 81 in FIG. 5, for example, the places where the fourth and fifth waves exhibit the respective maximum values have steep convex shapes, respectively, and it is distinctly seen that the places correspond to the fourth and fifth waves.

In the arithmetic average waveform 81A in FIG. 6, by contrast, the places where the fourth and fifth waves exhibit the respective maximum values do not clearly show that the places correspond to the fourth and fifth waves.

Also from this, it can be known that the arithmetic averaging number of the arithmetic average waveform 81 illustrated in FIG. 5 is sufficient, and that of the arithmetic average waveform 81A illustrated in FIG. 6 is insufficient.

As described above, the evoked potential measurement apparatus 1 of the disclosure includes: the measuring section 40 which acquires a physiological signal from the living body 100 of the subject; the signal processor 50 which produces a plurality of physiological signal waveforms based on the physiological signal acquired from the measuring section 40, and which identifies the arithmetic average waveform 70, 74, 77, 81, or 81A that is obtained by arithmetic averaging of the plurality of physiological signal waveforms, and information 71, 75, 78, 82, or 82A relating to arithmetic average dispersion; and the display 60 which displays at least the information 71, 75, 78, 82, or 82A relating to arithmetic average dispersion, and therefore an index for setting the arithmetic averaging number to an adequate number can be visualized.

The physiological signal acquired from the living body 100 is a minute signal, and includes noise due to the measurement environment and the like. Here, noise means a signal other than a required physiological signal, and includes an unnecessary physiological signal as well as disturbance noise. In order to remove noise and take out necessary waveforms, conventionally, arithmetic averaging is performed a predetermined number of times, and therefore an excess or shortage of adding processes easily occurs. Moreover, there is no configuration for providing an index for determining whether arithmetic averaging is performed a sufficient number of times or not. Conventionally, furthermore, a measurement result is determined to be good or not, while using an arithmetic average waveform as a material for determination, and therefore there is a possibility that a measurement result which is a false positive is erroneously determined as a good measurement result.

According to the disclosure, the apparatus includes the display 60 which displays at least the information 71, 75, 78, 82, or 82A relating to arithmetic average dispersion, and therefore an index for setting the arithmetic averaging number to an adequate number can be visualized. Since the information 71, 75, 78, 82, or 82A relating to arithmetic average dispersion is displayed, moreover, it is possible to visualize an index for determining whether noise components (noise) are sufficiently eliminated by performing arithmetic averaging or not, or whether the waveform of original signal components is obtained or not. The display of the information 71 or 82 relating to arithmetic average dispersion shows an index indicating that the arithmetic averaging number is sufficient, and hence it is possible to prevent unnecessary execution of arithmetic averaging from being performed. The display of the information 75 or 82A relating to arithmetic average dispersion shows also an index indicating that the arithmetic averaging number is not sufficient, and hence it is possible to continue arithmetic averaging in which there is a possibility that a false positive occurs, or that dispersion is excessively large and therefore the waveform of original signal components is not obtained. Consequently, a situation where the arithmetic averaging number is deficient can be prevented from occurring.

Since information relating to arithmetic average dispersion includes the 95% CI 71, 75, 78, 82, or 82A of physiological signal waveforms used in arithmetic averaging, an index for setting the arithmetic averaging number to an adequate number can be visualized.

The display 60 displays both the 95% CI 71, 75, 78, 82, or 82A and the arithmetic average waveform 70, 74, 77, 81, or 81A in a common area. Therefore, an index for setting the arithmetic averaging number to an adequate number can be visualized more clearly. When the wideness/narrowness of the width of the 95% CI 71, 75, 78, 82, or 82A is subjected to comparison in the whole range of the time axis, particularly, it is possible to visualize the pattern of the manner of superimposition of noise such as that a lot of noise is contained.

Moreover, information relating to arithmetic average dispersion includes the numerical information 73, and the display 60 displays both the numerical information 73 and the arithmetic average waveform 70, 74, 77, 81, or 81A in a common area. Therefore, numerical information for setting the arithmetic averaging number to an adequate number can be visualized. Consequently, an index for setting the arithmetic averaging number to an adequate number can be visualized more clearly.

Furthermore, an index for setting the arithmetic averaging number to an adequate number can be visualized by a program for causing a computer to realize: the function of producing a plurality of physiological signal waveforms based on the physiological signal which is converted to a digital signal; that of performing signal processing which identifies the arithmetic average waveform 70, 74, 77, 81, or 81A that is obtained by arithmetic averaging of the plurality of physiological signal waveforms, and the information 71, 75, 78, 82, or 82A relating to arithmetic average dispersion; and that of displaying at least the information 71, 75, 78, 82, or 82A relating to arithmetic average dispersion.

Second Embodiment, Determination Device

The physiological information measurement apparatus of the disclosure may have a configuration where the display 60 is not disposed. Hereinafter, an evoked potential measurement apparatus 1A which does not include a display, and which determines whether the arithmetic averaging number is sufficient or not will be described as a second embodiment with reference to FIGS. 2 to 7.

In the components of the evoked potential measurement apparatus 1A, components which are similar to those of the evoked potential measurement apparatus 1 are denoted by the same reference numerals, and duplicated description is omitted.

Figure 7:
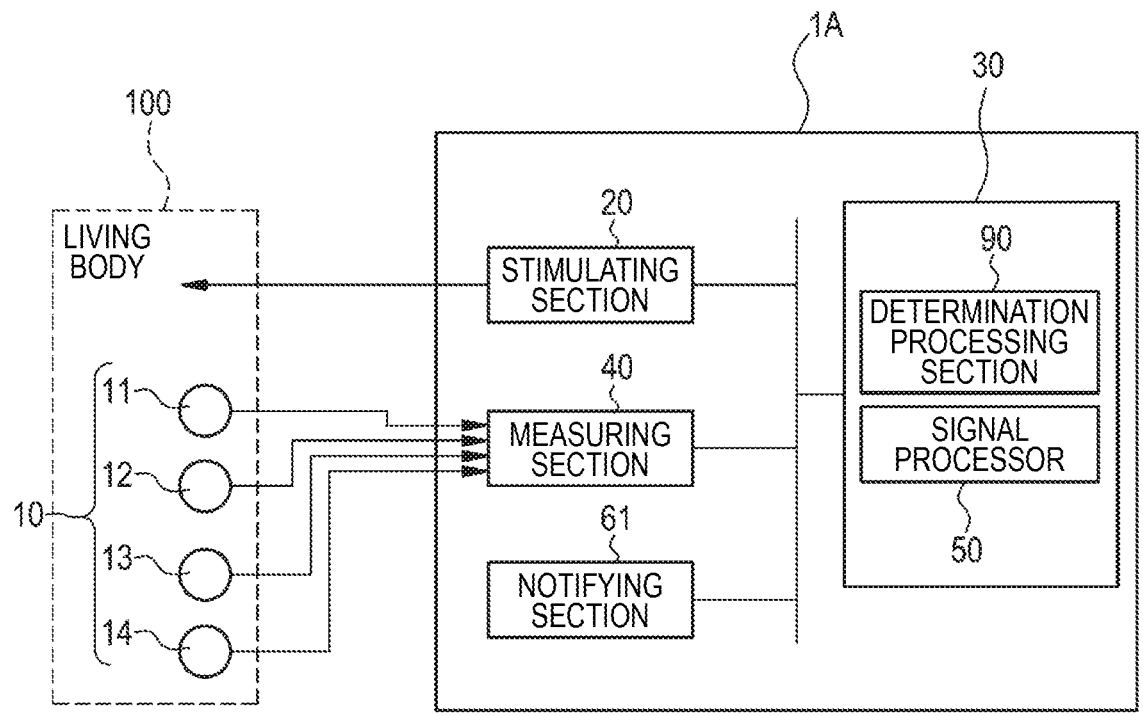
FIG. 7 is a functional block diagram of an evoked potential measurement apparatus which is another embodiment of the disclosure.

As shown in FIG. 7, the controller 30 of the evoked potential measurement apparatus 1A has a determination processing section 90. Moreover, the evoked potential measurement apparatus 1A has a notifying section 61 in place of the display 60 of the evoked potential measurement apparatus 1.

The determination processing section 90 acquires the arithmetic average waveform and the information relating to arithmetic average dispersion from the signal processor 50.

The determination processing section 90 is configured so as to determine whether the arithmetic averaging number is sufficient or not, based on at least the information relating to arithmetic average dispersion.

The determination processing section 90 may determine whether the arithmetic averaging number is sufficient or not, by means of comparison with a threshold.

For example, the determination processing section 90 statistically obtains the width of the 95% CI at which it can be determined that the arithmetic averaging number is sufficient, based on past measurement results, and sets the width as the threshold. The determination processing section 90 compares the threshold with the width of the 95% CI 71, 75, 78, 82, or 82A of FIGS. 2 to 6 (for example, the width 72 or 76, that of the 95% CI 78 at the place indicated by the reference numeral 79, or that of the 95% CI 78 at the place indicated by the reference numeral 80), thereby determining whether the arithmetic averaging number is sufficient or not.

Alternatively, the determination processing section 90 may determine whether the arithmetic averaging number is sufficient or not, based on the width of the 95% CI 71, 75, 78, 82, or 82A of FIGS. 2 to 6. The determination based on the width of the 95% CI 71, 75, 78, 82, or 82A may be performed by using various thresholds. For example, the determination processing section 90 calculates the mean value of the widths at points on the time axis (the mean value of the widths of the 95% CI 71, 75, 78, 82, or 82A in the whole range of the time axis) for each of the 95% CIs 71, 75, 78, 82, and 82A, and sets the calculated value as a threshold. Alternatively, the determination processing section 90 may set the maximum value of the 95% CI 71, 75, 78, 82, or 82A on the time axis, as a threshold.

The determination processing section 90 may have a configuration where a necessary arithmetic averaging number is estimated. For example, the estimation of a necessary arithmetic averaging number may be performed by estimating the number of remaining arithmetic averaging processes which are necessary until the arithmetic averaging number becomes sufficient. For example, the necessary remaining arithmetic averaging number may be estimated based on a change of arithmetic average dispersion in the case where the width of the 95% CI 71, 75, 78, 82, or 82A is monotonously (linearly) decreased in accordance with the increase of the arithmetic averaging number. In estimation using a linear graph relating to the width of the 95% CI, 71, 75, 78, 82, or 82A which is monotonously (linearly) decreased may be performed by calculating a prediction point where the narrowness of the width of the 95% CI 71, 75, 78, 82, or 82A at which it can be determined that the arithmetic averaging number is sufficient is attained, on an extension of the linear graph, and calculating the remaining arithmetic averaging number corresponding to the prediction point.

The determination processing section 90 can further determine whether the arithmetic averaging number is sufficient or not, by means of a statistical test due to test power analysis.

When the p-value, the effect size, and the test power are know namely, a necessary arithmetic averaging number can be obtained by the technique of the test power analysis. The p-value is conventionally 0.05. The test power is conventionally 0.8. The effect size can be identified in accordance with the degree of the difference between the null hypothesis and actual data. The effect size can be identified in accordance with the degree of the difference between flat waveform data (null hypothesis) in the case of no reaction waveform, and actual data (in FIGS. 2 to 4, data of the simulated measurement, and, in FIGS. 5 and 6, data of the actual measurement).

The determination processing section 90 calculates an adequate arithmetic averaging number by using the p-value=0.05, the effect size, and the test power=0.8, and sets the calculated value as a threshold. The determination processing section 90 can determine whether the arithmetic averaging number is sufficient or not, by determining whether the number of arithmetic averaging processes which have been performed in the past is equal to or larger than the threshold or not.

The determination processing section 90 produces a determination signal indicating that the arithmetic averaging number is sufficient, or that indicating that the arithmetic averaging number is not sufficient (the arithmetic averaging number is deficient). The determination processing section 90 outputs the produced determination signal to the notifying section 61.

The notifying section 61 is configured so as to perform notification depending on the determination signal. For example, the notifying section 61 may be configured by a speaker. In accordance with the determination signal indicating that the arithmetic averaging number is sufficient, the notifying section 61 outputs a short high-pitched sound indicating a normal operation. In accordance with the determination signal indicating that live arithmetic averaging number is not sufficient, the notifying section 61 outputs a sound indicating an alarm, such as a low-pitched buzzer sound.

Alternatively, the notifying section 61 may have a configuration in which visual notification is performed by an LED lamp, a display device, or the like.

The evoked potential measurement apparatus 1A may have a configuration where, when the arithmetic averaging number is sufficient, the acquisition of the physiological signal is stopped.

The determination processing section 90 can produce a signal indicating that the arithmetic averaging number is sufficient. In the case where a signal indicating that the arithmetic averaging number is sufficient is produced, the controller 30 can produce a measurement stop signal for stopping the measurement, and a stimulation application stop signal for stopping the stimulation application, in accordance with the signal indicating that the arithmetic averaging number is sufficient. The stimulation performed by the stimulating section 20 imposes a large burden on the subject. Therefore, the determination processing section 90 may have a configuration where only the stimulation application stop signal is produced.

In the operation of the evoked potential measurement apparatus 1A, the determination processing section 90 acquires the arithmetic average waveform 70, 74, 77, 81, or 81A, and the information 71, 75, 78, 82, or 82A relating to arithmetic average dispersion, from the signal processor 50. The determination processing section 90 determines whether the arithmetic averaging number is sufficient or not, based on the information 71, 75, 78, 82, or 82A relating to arithmetic average dispersion, and arithmetic average waveform 70, 74, 77, 81, or 81A which are acquired. The determination processing section 90 outputs a result of the determination whether the arithmetic averaging number is sufficient or not, to the notifying section 61. The notifying section 61 notifies live result of the determination whether the arithmetic averaging number is sufficient or not.

If the arithmetic averaging number is sufficient, the determination processing section 90 produces a signal indicating that the arithmetic averaging number is sufficient. In accordance with the signal indicating that the arithmetic averaging number is sufficient, the controller 30 produces the measurement stop signal and the stimulation stop signal. The controller 30 outputs the measurement stop signal to the measuring section 40, and the stimulation application stop signal to the stimulating section 20. In response to the input of the measurement stop signal, the measuring section 40 stops the acquisition of the physiological signal from the living body 100. In response to the input of the stimulation application stop signal, the stimulating section 20 stops the application of stimulation to the living body 100. Alternatively, the controller 30 causes the stimulating section 20 to stop the output of the control signal for applying stimulation to the living body 100.

Alternatively, the determination processing section 90 may have a configuration where the section acquires only the information 71, 75, 78, 82, or 82A relating to arithmetic average dispersion. Alternatively, the evoked potential measurement apparatus 1A may have a configuration where the stimulation application stop signal is not produced, and the acquisition of the physiological signal from the living body 100 is stopped in accordance with the measurement stop signal.

The notification by the notifying section 61 may not be performed, and the application of stimulation which is performed by the stimulating section 20 on the living body 100 may be stopped in accordance with the measurement result which is obtained from the determination processing section 90, and which indicates that the arithmetic averaging number is sufficient. Alternatively, in accordance with the measurement result which is obtained from the determination processing section 90, and which indicates that the arithmetic averaging number is sufficient, the execution of arithmetic averaging by the signal processor 50 may be stopped.

As described above, the evoked potential measurement apparatus 1A of the disclosure includes: the measuring section 40 which acquires a physiological signal from the living body 100; the signal processor 50 which produces a plurality of physiological signal waveforms based on the physiological signal acquired from the measuring section 40, and which identifies the arithmetic average waveform 70, 74, 77, 81, or 81A that is obtained by arithmetic averaging of the physiological signal waveforms, and the information 71, 75, 78, 82, or 82A relating to arithmetic average dispersion; and the determination processing section 90 which determines whether the arithmetic averaging number is sufficient or not, based on at least the information 71, 75, 78, 82, or 82A relating to arithmetic average dispersion, and therefore it is possible to know whether the arithmetic averaging number is sufficient or not.

The evoked potential measurement apparatus 1A stops the application of stimulation to the living body 100 in accordance with the determination that the arithmetic averaging number is sufficient, and therefore it is possible to prevent unwanted stimulation application from being performed.

Third Embodiment, Display and Determination Devices

The physiological information measurement apparatus of the disclosure may have a configuration where the apparatus includes a display and a determination device. Hereinafter, an evoked potential measurement apparatus 1B which includes the display 60 and the determination processing section 90 will be described with reference to FIGS. 2 to 6 and 8.

In the components of the evoked potential measurement apparatus 1B, components which are similar to those of the evoked potential measurement apparatuses 1 and 1A are denoted by the same reference numerals, and duplicated description is omitted.

Figure 8:
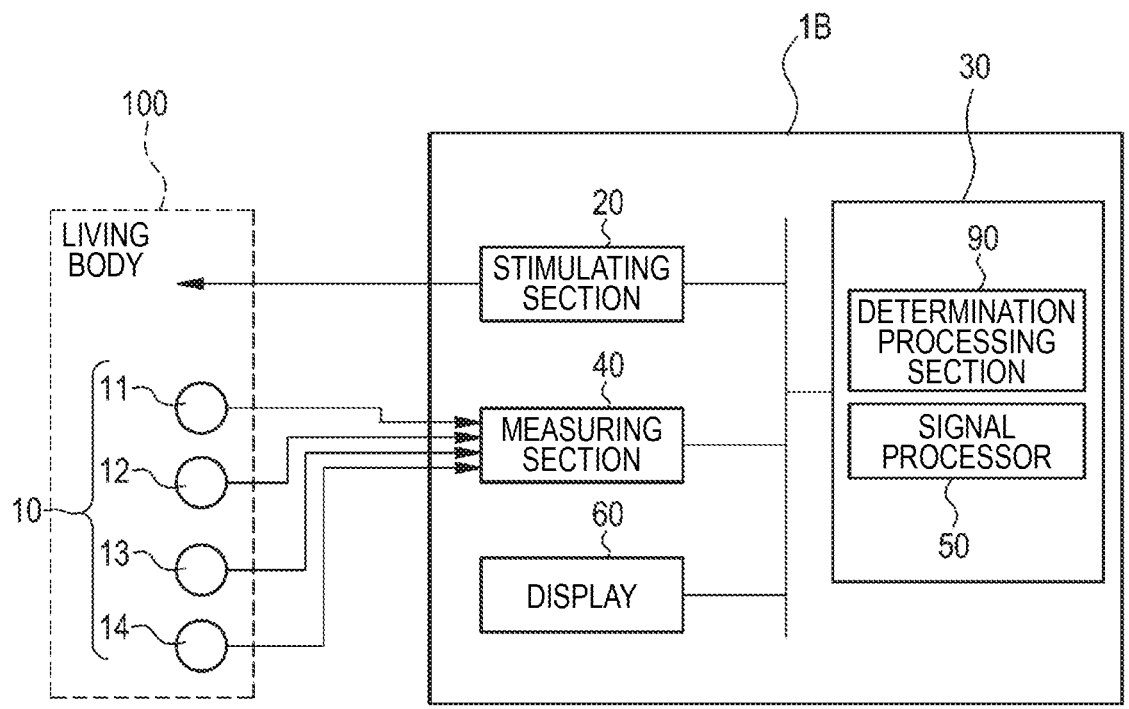
FIG. 8 is a functional block diagram of an evoked potential measurement apparatus which is a further embodiment of the disclosure.

As shown in FIG. 8, the evoked potential measurement apparatus 1B has the display 60. The controller 30 of the evoked potential measurement apparatus 1B includes the determination processing section 90.

The determination processing section 90 is configured so as to output the determination signal indicating that the arithmetic averaging number is sufficient, or that indicating that the arithmetic averaging number is not sufficient, to the display 60. The controller 30 produces a control signal such as the measurement stop signal and the stimulation application stop signal, in accordance with the determination signal which is produced by the determination processing section 90, and which indicates that the arithmetic averaging number is sufficient. The determination processing section 90 may estimate the number of remaining arithmetic averaging processes which are necessary until the arithmetic averaging number becomes sufficient, and output a result of the estimation to the display 60.

The display 60 is configured so as to display the information relating to arithmetic average dispersion. Similarly with the first embodiment, for example, the display 60 displays the 95% CI 71, 75, 78, 82, or 82A illustrated in FIGS. 2 to 6.

The display 60 may further display a result of the determination whether the arithmetic averaging number is sufficient or not and a result of the estimation in which the number of remaining arithmetic averaging processes that are necessary until the arithmetic averaging number becomes sufficient is estimated.

In accordance with the determination signal supplied from the determination processing section 90, the display 60 may further display information indicating whether the arithmetic averaging number is sufficient or not, in various modes. For example, the display modes may be formed by: characters of "Adding process is unnecessary," a bar graph of a color which is varied depending on whether the arithmetic averaging number is sufficient or not (when the arithmetic averaging number is insufficient, red, and, in the case of a sufficient arithmetic averaging number, black); and a gradation (color) region which is displayed in one section of the display 60 in accordance with the magnitude of the necessary remaining arithmetic averaging number.

As described above, the apparatus further includes the display for displaying at least the information 71, 75, 78, 82, or 82A relating to arithmetic average dispersion, and therefore an index for setting the arithmetic averaging number to an adequate number can be visualized.

The above-described embodiments are mere examples for facilitating understanding of the invention. The configurations of the embodiments may be adequately changed or improved without departing from the spirit of the invention. It is obvious that equivalents are included within the technical scope of the invention. In addition, the materials, shapes, forms, numbers, places, and the like of the components of the above-described embodiments are arbitrary and not limited insofar as the disclosure is achieved.

Although, in the above, the embodiments of an ABR evoked potential measurement apparatus have been described, the physiological information measurement apparatus of the disclosure is not limited to an ABR apparatus. The disclosure can be applied to various apparatuses which measure a minute physiological signal, and which perform an arithmetic averaging process. For example, the disclosure can be applied to a physiological information measurement apparatus which measures potentials of nerves and muscles, an electrocardiogram measurement apparatus, a SEP (Somatosensory Evoked Potential) apparatus, and the like. The stimulating section 20 may be configured so as to apply stimulation other than sound stimulation, for example, stimulation such as a current or a voltage.

Although the configuration where the arithmetic average waveform 70, 74, 77, 81, or 81A and the information 71, 75, 78, 82, or 82A relating to arithmetic average dispersion are output from the signal processor 50 to the display 60 or the determination processing section 90 is employed, the disclosure is not limited to the configuration. A configuration where the signal processor 50 outputs only the information 71, 75, 78, 82, or 82A relating to arithmetic average dispersion to the display 60 or the determination processing section 90 may be employed.

The arithmetic average waveform 70, 74, 77, 81, or 81A and the information 71, 75, 78, 82, or 82A relating to arithmetic average dispersion may be output from a section other than the signal processor 50.

The determination processing section 90 may acquire the information 71, 75, 78, 82, or 82A relating to arithmetic average dispersion, through a network such as the Internet, a local area network (LAN), or a wide area network (WAN).

Although, in the above, the embodiments in which the 95% CI is used as arithmetic average dispersion have been described, the confidence coefficient is not limited to 95%. For example, the confidence coefficient may be set to 99% (99% CI).

In order to realize the physiological information measurement apparatus of the disclosure by using software, the physiological information measurement program may be pre-installed in the memory (a storage section such as a ROM). Alternatively, the physiological information measurement program may be stored on a computer readable storage medium such as a magnetic disk (an HDD (Hard Disk Drive) or a floppy disk), an optical disk (a CD-ROM, a DVD-ROM, a Blu-ray (registered trademark) disk, or the like), a magneto-optical disk (an MD or the like), or a flash memory (an SD card, a USB memory, an SSD (Solid Disk Drive), or the like). In the alternative, when the physiological information measurement program which is stored in a storage medium is read by a disk drive or the like disposed in the physiological information measurement apparatus, the physiological information measurement program is installed in the memory.

Alternatively, the physiological information measurement program may be downloaded from a computer on a communication network, through a network interface. Also in the alternative, similarly, the downloaded program is installed in the memory.

What is claimed is:

1. A physiological information measurement apparatus comprising:
   a stimulus section configured to provide stimulus to a living body of a subject;
   a sensor configured to acquire physiological signals from the living body of the subject;
   a controller configured to:
      produce a physiological signal waveform by continuing to average the physiological signals acquired from the sensor for N times,
      acquire an arithmetic average dispersion of the physiological signal waveform, the arithmetic average dispersion being an index indicating a range in which the physiological signals are possible to occur,
      determine whether the N times of averaging is sufficient by comparing information related to the acquired arithmetic average dispersion of the physiological signal waveform with a threshold; and
      stop providing the stimulus and acquiring the physiological signals from the sensor, in response to determining that the N times of averaging is sufficient, and
   a display configured to display the physiological signal waveform on a screen,
   wherein the information related to the acquired arithmetic average dispersion is a width of a confidence interval of the physiological signal waveform.

2. The physiological information measurement apparatus according to claim 1, wherein the display is configured to display the confidence interval and the physiological signal waveform in a common area.

3. The physiological information measurement apparatus according to claim 1, wherein the arithmetic average dispersion includes numerical information, and the display is configured to display the numerical information and the physiological signal waveform in a common area.

4. The physiological information measurement apparatus according to claim 1, wherein the physiological signals are electroencephalogram signals.

5. A physiological information measurement apparatus comprising:
   a stimulus section configured to provide stimulus to a living body of a subject;
   a sensor configured to acquire physiological signals from the living body of the subject;
   a controller configured to:
      output a control signal to the stimulus section according to a configuration input value;
      produce a physiological signal waveform by continuing to average the physiological signals acquired from the sensor for N times,
      acquire an arithmetic average dispersion of the physiological signal waveform, the arithmetic average dispersion being an index indicating a range in which the physiological signals are possible to occur,
      determine whether the N times of averaging is sufficient by comparing information related to the acquired arithmetic average dispersion of the physiological signal waveform with a threshold; and
      stop providing the stimulus at the stimulus section and acquiring the physiological signals from the sensor, in response to determining that the N times of averaging is sufficient, and
   a display configured to display the physiological signal waveform on a screen,
   wherein the information related to the acquired arithmetic average dispersion is a width of a confidence interval of the physiological signal waveform.

6. The physiological information measurement apparatus according to claim 5, wherein the display is configured to display the confidence interval and the physiological signal waveform in a common area.

7. A non-transitory computer readable medium storing a physiological information measurement program that, when executed by a computer, causes the computer to execute a process comprising:
   providing, by a stimulus section, stimulus to a living body of a subject;
   acquiring, by a sensor, physiological signals from the living body of a subject;
   producing a physiological signal waveform by continuing to average physiological signals acquired from the living body of the subject for N times;
   acquiring an arithmetic average dispersion of the physiological signal waveform, the arithmetic average dispersion being an index indicating a range in which the physiological signals are possible to occur,
   determining whether the N times of averaging is sufficient by comparing information related to the acquired arithmetic average dispersion of the physiological signal waveform with a threshold;

stopping providing the stimulus at the stimulus section and acquiring the physiological signals from the sensor, in response to determining that the N times of averaging is sufficient, and displaying the physiological signal waveform on a screen, wherein the information related to the acquired arithmetic average dispersion is a width of a confidence interval of the physiological signal waveform.

8. The non-transitory computer readable medium according to claim 7, wherein the arithmetic average dispersion includes the confidence interval of the physiological signal waveforms.

9. The non-transitory computer readable medium according to claim 8, wherein, in the displaying process, the confidence interval and the physiological signal waveform are simultaneously displayed in a common display area.

* * * * *